United States Patent
Knepper

(10) Patent No.: US 8,011,366 B2
(45) Date of Patent: Sep. 6, 2011

(54) METHOD FOR ACCLIMATING A CPAP THERAPY PATIENT TO PRESCRIBED PRESSURE

(75) Inventor: Michael B. Knepper, Friedens, PA (US)

(73) Assignee: DeVilbiss Healthcare LLC, Somerset, PA (US)

( * ) Notice: Subject to any disclaimer, the term of this patent is extended or adjusted under 35 U.S.C. 154(b) by 1882 days.

(21) Appl. No.: 11/035,124

(22) Filed: Jan. 13, 2005

(65) Prior Publication Data

US 2005/0166922 A1 Aug. 4, 2005

Related U.S. Application Data

(60) Provisional application No. 60/541,792, filed on Feb. 4, 2004.

(51) Int. Cl.
*A62B 7/02* (2006.01)
*A61M 16/00* (2006.01)

(52) U.S. Cl. .............. 128/204.23; 128/204.26

(58) Field of Classification Search ............ 128/204.26, 128/203.14, 204.18, 204.21, 204.23

See application file for complete search history.

(56) References Cited

U.S. PATENT DOCUMENTS

| 5,117,819 | A | 6/1992 | Servidio et al. | 128/204.18 |
|---|---|---|---|---|
| 5,148,802 | A | 9/1992 | Sanders et al. | 128/204.18 |
| 5,199,424 | A | 4/1993 | Sullivan et al. | 128/204.18 |
| 5,313,937 | A | 5/1994 | Zdrojkowski | 128/202.22 |
| 5,433,193 | A | 7/1995 | Sanders et al. | 128/204.18 |
| 5,503,146 | A | 4/1996 | Froelich et al. | 128/204.23 |
| 5,551,419 | A | 9/1996 | Froelich et al. | 128/204.23 |
| 6,532,960 | B1 * | 3/2003 | Yurko | 128/204.26 |

* cited by examiner

*Primary Examiner* — Danton DeMille

(74) *Attorney, Agent, or Firm* — Dennis Carleton; Fox Rothschild LLP

(57) ABSTRACT

A method for acclimating a CPAP therapy patient to a prescribed pressure while the patient falls asleep. During an initial startup period, the CPAP apparatus applies a therapeutic IPAP pressure to the patient's airway and a lower initial EPAP pressure to the patient's airway. The EPAP pressure is ramped up to the IPAP pressure over a sufficient time for the patient to fall asleep. In a modified embodiment, both the initial IPAP pressure and the initial EPAP pressure are less than the prescribed therapeutic pressure. The IPAP and EPAP pressures are then independently ramped up to the prescribed therapeutic pressure.

8 Claims, 2 Drawing Sheets

METHOD FOR ACCLIMATING A CPAP THERAPY PATIENT TO PRESCRIBED PRESSURE

CROSS-REFERENCE TO RELATED APPLICATIONS

Applicants claim priority to U.S. Provisional Patent Application Ser. No. 60/541,792 filed Feb. 4, 2004.

STATEMENT REGARDING FEDERALLY SPONSORED RESEARCH OR DEVELOPMENT

Not Applicable.

TECHNICAL FIELD

The invention relates to a method for acclimating a patient to CPAP therapy when the CPAP apparatus is first turned on and the patient has not yet fallen asleep.

BACKGROUND OF THE INVENTION

The application of a continuous positive airway pressure (CPAP) to a patient's respiratory system is a frequently used therapy for treating sleep disorders such as obstructive sleep apnea. Typically, positive air pressure is applied to the patient's airway through either a nasal mask or a nasal cannula. Apnea is commonly caused by the upper airway being blocked or collapsing during sleep. With CPAP, an inspiratory positive airway pressure (IPAP) applied to the patient is set to a pressure which expands or inflates the airway sufficiently to prevent its blockage during inspiration. The lowest effective IPAP pressure for a patient may be determined through titration in a sleep clinic or by using CPAP apparatus which is programmed to automatically adjusts the applied pressure up and down in response to the occurrence and the absence of sleep events until the events cease. The pressure is increased and decreased while monitoring for abnormal sleep events until the lowest effective IPAP pressure is determined.

CPAP therapy is effective only so long as the patient complies with the prescribed therapy. As many as 20% to 40% of the patients for which CPAP therapy is prescribed fail to adhere to the prescribed therapy due to discomfort. The most frequent source of discomfort is with the nasal mask. A second source of discomfort can result from the additional work of breathing against the applied CPAP pressure. This is particularly noticeable when the CPAP pressure is first applied while the patient is still awake. Inspiration is not a problem with a positive airway pressure. However, there is additional effort in exhaling against the positive airway pressure. One solution for reducing discomfort has been to provide the CPAP apparatus with a soft start. When the apparatus is initially turned on, a relative low positive pressure is applied to the patient's airway. This pressure is below the prescribed pressure necessary for preventing abnormal respiratory events. However, abnormal respiratory events are generally not a problem while the patient is awake. Over a programmed period of time such as 20 or 30 minutes, the applied pressure is gradually increased or ramped up to the prescribed therapeutic pressure. Some CPAP apparatus provides a constant low pressure for a period of time prior to increasing to the prescribed therapeutic pressure. The soft start helps the patient to fall asleep before the pressure is increased to the therapeutic level.

For standard CPAP apparatus, the IPAP pressure and the expiratory positive airway pressure (EPAP) are substantially the same. Another method for reducing discomfort from exhaling against the therapeutic pressure is to provide bilevel CPAP therapy. For obstructive sleep apnea, most airway blockages occur only during inspiration. In a bilevel system, the CPAP apparatus is controlled to increase the applied IPAP pressure to the prescribed therapeutic level in response to sensing the beginning of inspiration and to decrease the applied EPAP pressure to a lower, more comfortable level in response to sensing the beginning of expiration. This reduces the effort and discomfort of exhaling against the prescribed pressure. Bilevel CPAP therapy is particularly useful for patients who require a high IPAP pressure for preventing abnormal sleep events. However, for some patients, bilevel CPAP therapy may not be as effective as applying a constant therapeutic pressure to the patient.

BRIEF SUMMARY OF THE INVENTION

The invention is directed to a method for acclimating a CPAP therapy patient to the prescribed pressure during the time the patient is falling asleep. When the CPAP apparatus is first turned on, a bilevel positive pressure is applied to the patient's respiratory system. The pressure alternates between an IPAP pressure set at the patient's prescribed therapeutic pressure when the patient inhales and a predetermined low EPAP pressure when the patient exhales. After a programmed delay, the EPAP pressure is gradually increased or ramped up to the prescribed pressure, at which time a constant prescribed pressure is applied to the patient during both inspiration and expiration to provide maximum therapy. The delay may be set to an estimated time required for the patient to fall asleep. The ramp for increasing the EPAP pressure may be linear or may be at other desired slopes, such as exponential. Also, the EPAP pressure may be maintained at a set low level for a set period of time before the EPAP pressure begins to ramp up to the level of the IPAP pressure.

In a modified embodiment, a CPAP system is provided in which the initial IPAP pressure also is reduced below the prescribed pressure, but to a pressure higher than the initial EPAP pressure. Both the IPAP and the EPAP pressures are gradually increased at programmed rates to the therapeutic pressure. The rates at which the IPAP and EPAP pressures are increased may be the same, or may be different, and may be selected based on the patient's needs. Optionally, delays may be provided before beginning the IPAP and EPAP pressures. In a further modified embodiment, both the IPAP and the EPAP pressures are initially set to the same lower pressure and the IPAP pressure is ramped up at a faster rate than the EPAP pressure so that the IPAP pressure reaches the prescribed therapeutic pressure before the EPAP pressure.

Various objects and advantages of the invention will become apparent from the following detailed description of the invention and the accompanying drawings.

DETAILED DESCRIPTION OF THE INVENTION

Program controlled CPAP apparatus is well known in the art. CPAP apparatus is commercially available for treating obstructive sleep apnea and other abnormal sleep events. The apparatus is programmed to apply a prescribed positive airway pressure to a patient's respiratory system while the patient sleeps. In one form of the program controlled CPAP apparatus, the pressure is reduced for a period of time while the patient falls asleep. This apparatus may be controlled to initially apply a pressure to the patient's airway which is below the prescribed therapeutic pressure and to ramp up the pressure to the prescribed level over a set period of time. Alternately, the apparatus may maintain the initial low pressure for a first period of time and then ramp up the pressure to the prescribed level over a second period of time.

CPAP apparatus has also been operated in a bilevel mode. In this mode, the apparatus detects when the patient begins to inhale and when the patient begins to exhale, generally by monitoring changes in the mass air flow from the CPAP apparatus to the patient, or by monitoring changes in the air pressure applied to the patient as the patient breathes, or by monitoring changes in both air flow and pressure. The apparatus is programmed to apply the prescribed therapeutic pressure (the IPAP pressure) when the patient inhales and to reduce the pressure when the patient exhales (the EPAP pressure). It is known that the bilevel CPAP apparatus may be started with the IPAP pressure set at or near the lower EPAP pressure, and that the IPAP pressure may be increased at a programmed rate to the prescribed pressure over a period of time while the patient falls asleep.

In both CPAP apparatus in which the IPAP and EPAP pressures are substantially the same and bilevel CPAP apparatus, during the initial reduced pressure startup period, the prescribed therapeutic pressure is not applied during the startup period. Nor are the IPAP pressure and the EPAP pressure optimized for the specific needs of the patient.

The invention is directed to methods for controlling the IPAP and EPAP pressures during an initial period while a patient on CPAP therapy falls asleep to acclimate the patient to the prescribed pressure. The invention may be implemented by modifying programming which controls existing CPAP and bilevel CPAP apparatus.

Figure 1:
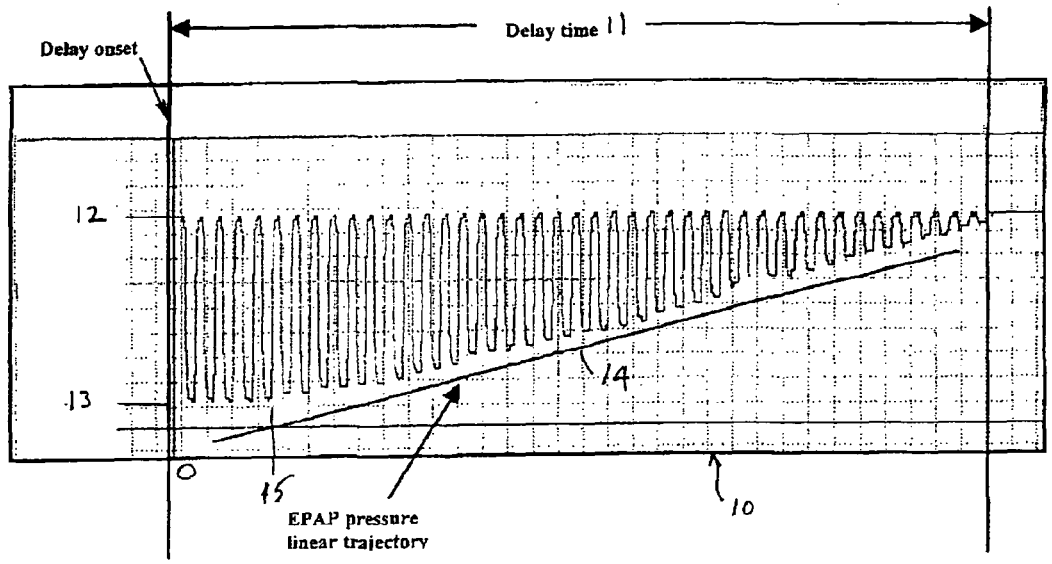
FIG. 1 is a graph showing start up of CPAP apparatus according to a first embodiment of the invention in which the IPAP pressure is maintained substantially constant at the prescribed therapeutic pressure while the EPAP pressure is ramped up from a low level to the level of the IPAP pressure over a preset period of time.

Referring to FIG. 1, a graph 10 is shown in which the Y axis represents the pressure applied to the patient's airway and the X axis represents time, with 0 on the X axis representing when the a startup interval for the CPAP apparatus begins. Startup occurs for a delay time 11. Reference 12 marks the prescribed therapeutic pressure for the patient, and reference 13 marks the initial EPAP pressure. During startup, the CPAP apparatus is operated in a bilevel mode wherein the IPAP pressure is always maintained at the prescribed therapeutic level 12. The EPAP pressure initially starts at the low level 13 and is gradually ramped up to the IPAP level 12 over the delay time 11. With this mode of operation, the patient receives the prescribed therapeutic pressure 12 during inspiration as soon as the CPAP apparatus is turned on. However, the work of exhaling against the higher IPAP pressure is reduced during the delay time 11 to increase patient comfort. The delay time is set to a time sufficient for the patient to fall asleep, and may be different for different patients. After the delay, the IPAP and EPAP pressures remain at the full prescribed therapeutic pressure. This startup process may be particularly effective for patients who require higher IPAP pressures for preventing the occurrence of apnea or other abnormal events.

The bilevel operation may be controlled in different ways. In normal bilevel operation, the applied pressure is increased in response to detecting inhalation and is decreased in response to detecting exhalation. According to one aspect of the invention, the prescribed IPAP pressure is set as the default pressure. The CPAP apparatus may be operated to detect only the inhalation to exhalation transition. In response to detecting exhalation, the pressure is reduced to the EPAP pressure for a set time interval before returning to the default IPAP pressure. If desired, the rate at which the pressure returns to the default pressure can be set as a defined function. Alternately, only the exhalation to inhalation transition may be detected for increasing the applied pressure from the EPAP level to the IPAP level. After a preset time, the pressure can be returned to the EPAP level.

In FIG. 1, the EPAP pressure generally follows a linear ramp or trajectory 14 once the EPAP pressure begins to rise at a time 15. However, the EPAP pressure may be set to follow a trajectory determined by a logarithmic function or other function which decays with time towards the IPAP pressure during the delay time 11. The EPAP ramp or trajectory 14 may start when the CPAP apparatus is first turned on, or after a delay.

Figure 2:
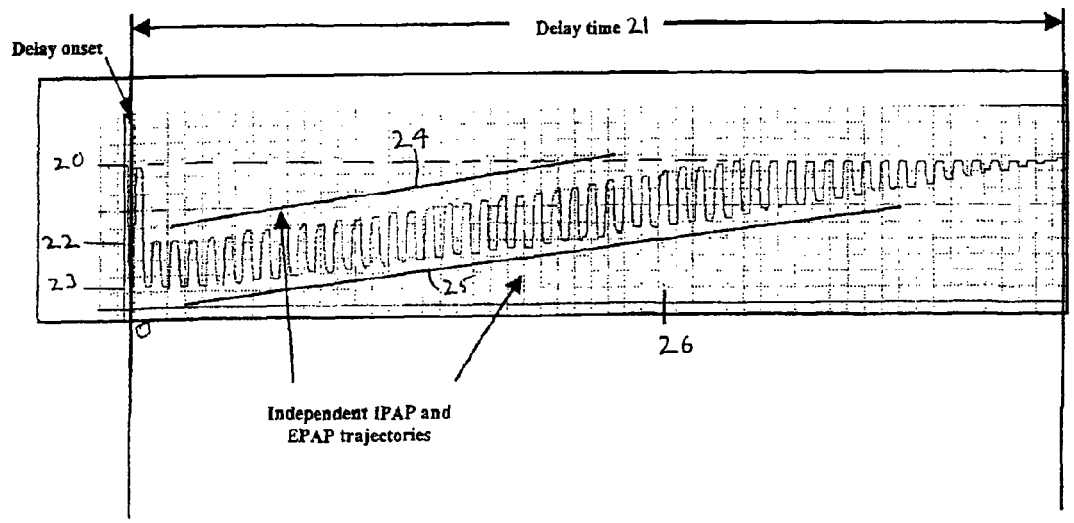
FIG. 2 is a graph showing start up of CPAP apparatus according to a modified embodiment of the invention in which both the IPAP pressure and a lower EPAP pressure are ramped up to the prescribed therapeutic pressure over a preset period of time.

FIG. 2 shows a modified embodiment of the invention wherein both the IPAP and the EPAP pressures are ramped up from initial levels to a prescribed therapeutic pressure 20 during a delay time 21. The IPAP pressure has an initial level 22 and the EPAP pressure has an initial level 23. During the startup delay time, the IPAP pressure is ramped up to the pressure 20 along a trajectory 24 and the EPAP pressure is ramped up to the therapeutic pressure 20 along a trajectory 25 which is independent from the trajectory 24. The IPAP pressure reaches the prescribed pressure 20 at a time 26 prior to the end of the delay time 21, while the EPAP pressure does not reach the prescribed pressure 20 until the end of the delay time 21. This delay function should be effective in providing a patient the comfort of lower EPAP pressures during exhalation and initially lower IPAP pressures while falling asleep. A smooth transition is provided between the delay phase before sleep and the actual CPAP therapy during sleep. Once the patient is sleeping and the delay time 21 has lapsed, both the IPAP and the EPAP pressures are held at the prescribed therapeutic pressure 20. If the CPAP apparatus is of the auto adjust type which modifies the applied airway pressure based on the presence and absence of abnormal sleep events, then the prescribed pressure will be the pressure currently set by the auto adjust controller.

In FIG. 2, the trajectories 24 and 25 are spaced apart and are shown as being generally linear and parallel. It should be appreciated that the trajectories 24 and 25 need not be linear or parallel. The trajectories 24 and 25 may be custom set for the needs of a particular patient to optimize the pressures to reduce or eliminate the occurrence of sleep events while the patient falls asleep while providing the best possible patient comfort. It should be noted that the IPAP trajectory 24 will always reach the prescribed pressure 20 either prior to or at the same time that the EPAP trajectory 25 reaches the prescribed pressure so that the EPAP pressure never exceeds the IPAP pressure.

Figure 3:
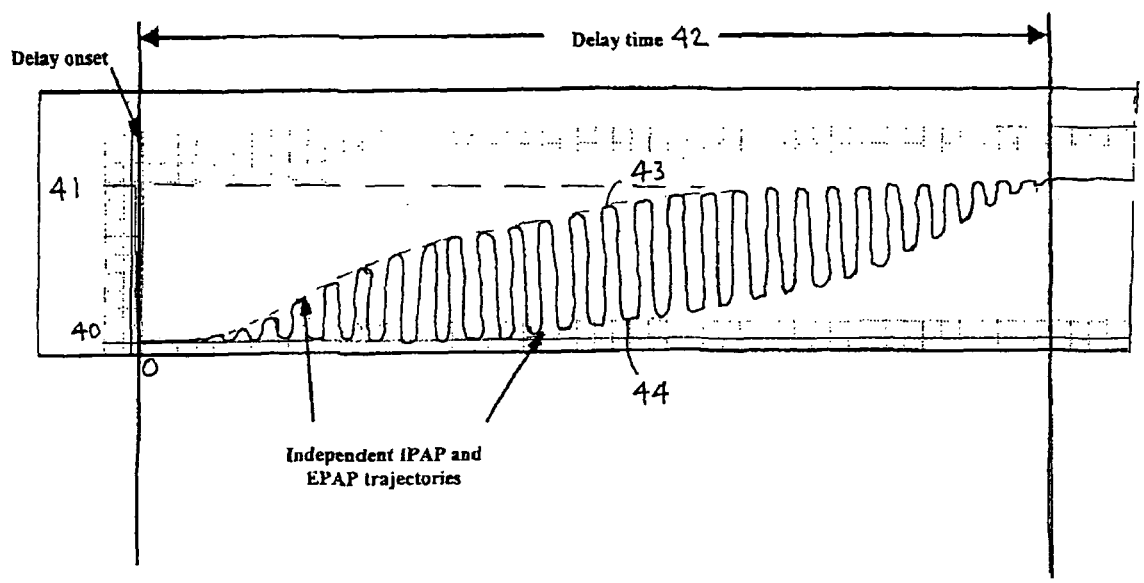
FIG. 3 is a graph showing start up of CPAP apparatus according to a further modified embodiment of the invention in which both the IPAP and the EPAP pressures start out at the same low level and are ramped up to the prescribed pressure at different rates.

FIG. 3 shows a further modified embodiment of the invention wherein both the IPAP and the EPAP pressures start at the same low initial pressure 40 and both end at the constant prescribed pressure 41 at the end of a startup delay time 42.

However, the IPAP and EPAP pressures follow different trajectories, as illustrated. The IPAP pressure increases along a trajectory 43 faster than the EPAP pressure increases on a trajectory 44, which is maintained at or near the initial pressure 40 for a greater portion of the delay time than the IPAP pressure. At the end of the delay time 42 when the patient is presumed to be asleep, the constant prescribed pressure 41 is maintained on the patient's airway during both inhalation and exhalation. The IPAP and the EPAP pressures may be held at the low initial pressure 40 for a period of time before starting the IPAP ramp 43, based on the patient's comfort needs.

It will be appreciated that the highest IPAP pressure may be applied for only a portion of the patient's inspiration time and that the lowest EPAP pressure may be applied for only a portion of the patient's expiration time. Various modifications and changes may be made to the above described preferred embodiment of a method for acclimating a patient to CPAP therapy without departing from the scope of the following claims.

The invention claimed is:

1. A method for controlling startup of CPAP apparatus which applies an IPAP pressure to a patient's airway during inhalation and an EPAP pressure to the patient's airway during exhalation, said method comprising the steps of applying a therapeutic IPAP pressure to the patient's airway during a startup period, and at the beginning of the startup period applying an EPAP pressure below the therapeutic IPAP pressure to the patient's airway and increasing the EPAP pressure to the therapeutic IPAP pressure during the startup period.

2. A method for controlling startup of CPAP apparatus, as set forth in claim 1, and wherein the EPAP pressure is maintained at a predetermined pressure for an initial portion of the startup period and is then increased over time to the prescribed pressure.

3. A method for controlling startup of CPAP apparatus, as set forth in claim 1, and further including the step of maintaining the IPAP pressure and the EPAP pressure at the same level after the startup period.

4. A method for controlling startup of CPAP apparatus which applies an IPAP pressure to a patient's airway during inhalation and an EPAP pressure to the patient's airway during exhalation, the patient having a predetermined therapeutic airway pressure for reducing or eliminating the occurrence of abnormal sleep events, said method comprising the steps of initially applying an IPAP pressure to the patient's airway which is less than the predetermined therapeutic pressure and applying an EPAP pressure to the patient's airway which is no greater than the IPAP pressure, during a startup period increasing the IPAP pressure along a first trajectory to the predetermined therapeutic pressure, during the startup period increasing the EPAP pressure along a second trajectory to the predetermined therapeutic pressure, wherein said second trajectory is different from said first trajectory, and wherein the EPAP pressure does not exceeds the IPAP pressure during the startup period.

5. A method for controlling startup of CPAP apparatus, as set forth in claim 4, and wherein the IPAP pressure initially applied to the patient's airway is greater than the EPAP pressure initially applied to the patient's airway.

6. A method for controlling startup of CPAP apparatus, as set forth in claim 5, and wherein the IPAP pressure is increased to the predetermined therapeutic pressure before the EPAP pressure reaches the predetermined therapeutic pressure.

7. A method for controlling startup of CPAP apparatus, as set forth in claim 4, and wherein the IPAP pressure initially applied to the patient's airway is the same pressure as the EPAP pressure initially applied to the patient's airway 8. A method for controlling startup of CPAP apparatus, as set forth in claim 7, and wherein the IPAP pressure is increased to the predetermined therapeutic pressure before the EPAP pressure reaches the predetermined therapeutic pressure.

* * * * *